United States Patent
Kildea, Jr.

(10) Patent No.: US 6,231,340 B1
(45) Date of Patent: May 15, 2001

(54) ENDODONTIC INSTRUMENT

(76) Inventor: Patrick M Kildea, Jr., 4701 Sangamore Rd., Bethesda, MD (US) 20816

( * ) Notice: Subject to any disclaimer, the term of this patent is extended or adjusted under 35 U.S.C. 154(b) by 0 days.

(21) Appl. No.: 08/935,107

(22) Filed: Sep. 29, 1997

(51) Int. Cl.[7] ............................ A61C 3/00; A61C 5/02
(52) U.S. Cl. ................................. 433/147; 433/102
(58) Field of Search ............................ 433/102, 141, 433/146, 147

(56) References Cited

U.S. PATENT DOCUMENTS

| | | | |
|---|---|---|---|
| 797,684 | * | 8/1905 | Harper ................................. 433/147 |
| 1,187,497 | * | 6/1916 | Canfield .......................... 433/147 X |
| 1,327,477 | * | 1/1920 | Ivory ................................ 433/147 X |
| 1,406,143 | * | 2/1922 | Bates ............................... 433/147 X |
| 3,471,929 | * | 10/1969 | Boone .............................. 433/147 X |
| 4,364,730 | * | 12/1982 | Axelsson ......................... 433/147 X |
| 4,580,979 | * | 4/1986 | Leonard ........................... 433/147 X |
| 4,992,048 | * | 2/1991 | Goof ................................... 433/102 |
| 5,092,769 | * | 3/1992 | Reiter et al. .................... 433/147 X |

* cited by examiner

Primary Examiner—Nicholas D. Lucchesi
(74) Attorney, Agent, or Firm—Rodger H. Flagg

(57) ABSTRACT

The endodontic instrument disclosed herein comprises a back portion sized to be comfortably received within a user's hand, a middle portion which is smaller in cross-section than the back portion, and a threaded front portion of larger cross sectional size than the middle portion. The middle portion may be straight along the centerline of the back portion, or may be partially radiused from fifteen to forty-five degrees from the centerline of the back portion. A transverse aperture extends through the threaded front portion. The transverse aperture is sized to closely receive the shaft of a dental tool from either side of the transverse aperture. A nut is threadably received on the threaded front portion, and the nut is rotated to tighten the nut against the shaft of the selected tool to secure the selected tool to the endodontic instrument. The back portion and the nut are preferably textured to improve the gripping surface.

24 Claims, 1 Drawing Sheet

ENDODONTIC INSTRUMENT

FIELD OF THE INVENTION

The present invention relates to endodontic tools, and more specifically to an improved endodontic handle, useable with numerous attachments, for cleaning teeth, performing root canals and related dental procedures.

BACKGROUND OF THE INVENTION

Endodontics is the branch of dentistry concerned with tooth diseases. Tooth disease can affect a person's general health and, conversely, illness can cause dental problems. A common dental problem is tooth decay or cavities. Tooth decay is generally caused by acids secreted by bacteria that adhere to a tooth's surface in a film called dental plaque. The acids cause minerals in the tooth enamel to soften, allowing bacteria and food particles to enter the tooth. If left untreated, decay can eventually lead to loss of the entire tooth.

Periodontal diseases involve the gingiva, or gums, and underlying structures, and they usually affect adults. Improper dental hygiene and lack of professional care promote periodontal disease. Periodontitis is a bacterial inflammation at the base of the teeth including the ligament that holds the teeth to the bone and the bone itself. The main cause is the buildup of tartar, which irritates the gums and permits bacteria to become established. If untreated, the gums recede, the bone leeches away, and the teeth fall out. Periodontitis is the major cause of tooth loss in adults.

Prophylaxis, or prevention of tooth decay, involves thorough cleaning of the teeth by a dental hygienist. Abrasives and scraping tools are used to remove tartar and other material from the teeth. Tartar is formed from mineral salts that react with dental plaque and saliva to form crusty areas that cannot be removed by daily brushing. This buildup of tartar encourages tooth decay and irritates the gums.

A dental examination generally starts with X rays of the teeth. The X-rays are used by the dentist to detect decay or other problems, such as an impacted tooth. An impacted tooth is one that is unable to erupt normally through the gum. The condition of the gums and other soft tissue is also inspected, and previous dental work such as fillings, inlays, and bridges are examined for irregularities that need correcting.

When a tooth is found to have a cavity, the decay is removed with a high-speed drill. After decay removal, the cavity is filled. Usually the area where the work is to be done is numbed first with a local anesthetic such as Novocain or procaine, and sometimes the anesthetic gas nitrous oxide is used. The material used to fill the cavity may be an inert, nontoxic mixture of silver and mercury, or it may be gold, porcelain, or plastic. This is packed tightly into the cavity and the outer surface is smoothed.

When decay reaches the pulp of a tooth and inflames the nerve, causing pain and infection, root canal, or endodontic, treatment becomes necessary. The treatment procedure entails pulp removal from the tooth and replacement with metal, cement, or some other material A crown, gold inlay, or filling material is used to close the cavity. Crowns, or caps, cover the entire tooth. These are used when the enamel of a tooth has been removed. Crowns are made of porcelain, plastic, or gold.

The drilling, filling, packing and smoothing procedures require individual specialized tools and attachments. As a result the dentist may change tools and attachments often during a typical visit. As a result of the requirement for numerous individual tools and attachments, the dentist's office becomes cluttered with numerous tools. The dentist is forced to fumble for a specific tool, create extra space for a tool set up and maintain duplicate tools for each dentist chair used in the office and incur the expense of duplicate tools. In addition, the many dental tools may have different handles causing the dentist to tax his or her dexterity in different ways when using the different handles. As a result, a need has arisen for a dental tool with a single handle that can easily accommodate numerous dental attachments. The tool should be small enough to fit in a dentist's hand, have a precise shape so as to reach into the numerous crevices of the mouth, have a universal affixing system to securely hold small attachments in order to conserve office space, be useable in numerous offices, be cost effective, and have the structural integrity to allow the dentist to effectively use the variety of dental attachments.

U.S. Pat. No. 4,490,410 discloses a dental tool holder including a variety of shock absorbing internal devices to reduce vibration of the tool during use.

U.S. Pat. No. 5,228,852 discloses an elongated hand piece assembly used with a dental laser for facilitating precisely aligned and controlled use of the laser during dental procedures.

U.S. Pat. No. 5,236,358 discloses a dental tool having an opening at a front end for receiving an elongated abrasive dental attachment, wherein the attachment has a maximum diameter of less than 0.014 inches.

While all of the above identified U.S. patents disclose apparatus and methods which adequately perform the functions for which they were intended, none of them disclose an apparatus and method for easily, quickly and efficiently interchanging between dental attachments. Therefore, there is a need for a single tool which facilitates interchange between a plurality of dental attachments while providing the dentist with a familiar grip and shape.

SUMMARY OF THE INVENTION

Therefore, what is needed is a dental tool: having a single elongated Shaped handle for reaching into a patient's mouth; having the structural integrity to provide the dentist with effective use of the numerous dental attachments; and having the capability of holding and accommodating numerous dental attachments.

These objects and advantages are accomplished by the present invention, wherein a dental tool is provided having an elongated handle. The handle has numerous gripping areas. A first area used mostly for heavy and coarse use of a dental attachment. A second area is used mostly for fine and precise use of a dental attachment.

The dental tool includes a front portion having a transverse attachment aperture extending transversely through the front portion. The front portion is threaded to receive a threaded nut thereon The shaft of a selected dental tool is inserted into the transverse attachment aperture and releasably secured to the front portion by threadably biasing the nut against the shaft of the selected dental tool. The nut is preferably textured for ease of grasping and tightening the nut against the shaft of the selected dental tool with finger pressure. When the dentist wishes to change dental tool attachments, the dentist simply rotates the nut to bias the nut away from the shaft of the dental tool. The current dental tool attachment may then be removed from the transverse attachment aperture, in preparation for insertion of a different dental tool attachment.

The above mentioned features and objects of this invention, and the manner of attaining them will be best understood by reference to the following description of an embodiment of the invention, when considered in conjunction with the accompanying drawings.

DESCRIPTION OF PREFERRED EMBODIMENTS

Figures 1, 2:
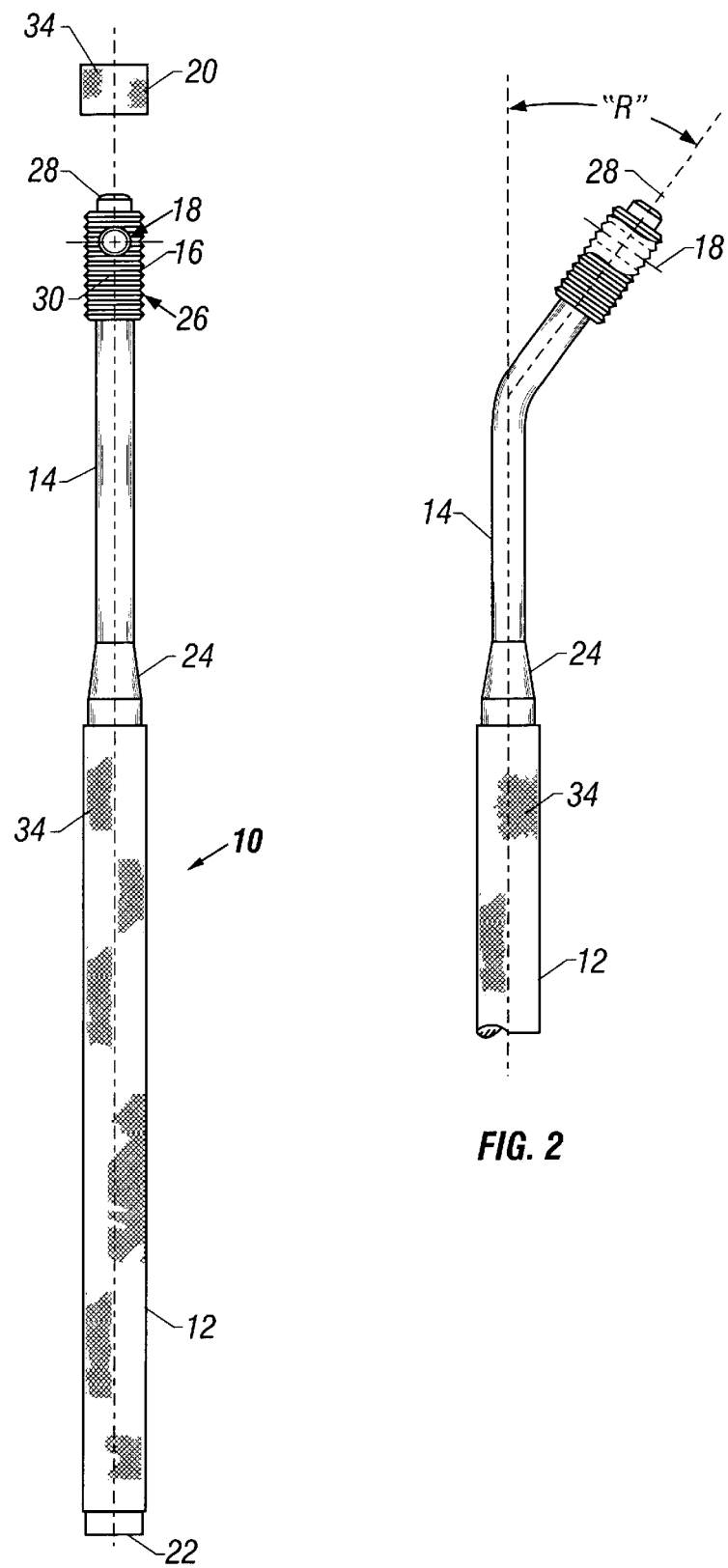
FIG. 1 is an exploded top view of the present invention.
FIG. 2 is a view of a forward segment of the handle showing a radiused portion of the present invention.

The structure and operation of our invention together with further objects and advantages may be better understood from the following description given in connection with the accompanying drawings, in which FIG. 1 depicts an exploded top view of a preferred embodiment of the present invention. As shown, the present invention comprises a handle 10 having a back portion 12, middle portion 14, and a front portion 16. The front portion is threaded 30 to threadably receive a nut 20 thereon. Preferably, the front portion 16 is threaded as a ¼-40 UNS-2A thread, extending one half inch long.

The shaft of a dental tool attachment (not shown), is inserted into a transverse aperture 18 extending through the front portion 16 of the handle apparatus 10. The dental attachment is releasably secured within the transverse aperture 18 by means of a nut 20 which is selectively tightened or loosened on the threaded 30 front portion 16. While the nut 20 is shown in exploded view in FIG. 1, the nut 20 need not be removed from the threaded front portion 16. The transverse aperture 18 extends through the threaded 30 front portion 16, so that the nut 20 may be threadably biased against the shaft of the dental tool attachment, to selectively releasably secure the dental tool attachment to the handle apparatus 10. In this way, numerous dental attachments may be selectively releasably secured to the handle apparatus 10.

The back portion 12 of the handle apparatus 10 has a generally elongated cylindrical shape, which preferably has a textured gripping surface 32 to facilitate gripping by a user's human hand while positioning of the front portion 16 of the handle apparatus 10 within a patient's mouth. The textured gripping surface 32 may be knurled, ribbed or otherwise treated to improve the finger gripping surface. The back portion 12 of the handle apparatus 10 is preferably cylindrical in cross-sectional shape, and preferably about four inches long. Other shapes and sizes may also be used without departing from the spirit of this disclosure, nor from the scope of the following claims. The back portion 12 is griped by the user when gross placement and application of the selected dental attachment is desired. By gripping the back portion 12, the user can apply force, in a particular direction, through the front portion 16, and the dental attachment to cause the dental attachment to forcefully contact and engage a portion of the inside of the patient's mouth. The force applied by the user can be in a single or in multiple directions as may be required by one skilled in the dentistry art.

The back portion 12 of the handle apparatus 10 has a handle end 22 which is preferably inclined, tapered or radiused to avoid a sharp edge thereon. The middle portion 14 of the handle apparatus 10 is preferably of a reduced cross sectional area for ease of insertion and manipulation within the patient's mouth. The transition between the back portion 12 and the middle portion 14 is preferably tapered 24. The middle portion 14 may extend straight from the centerline of the back portion, as shown in FIG. 1, or may be radiused as shown in FIG. 2, to suit design or manufacturing preference. The cross sectional area of the middle portion 14 may be of any desired shape, such as cylindrical, oval or multisided to suit manufacturing preference. The back portion 12 of the handle apparatus 10 provides the user with a place to exert controlled forward as well as rotational force on the handle 10.

The front portion 16 is preferably larger in cross sectional area than the middle portion 14. The transition between the middle portion 14 and the front portion 16 is preferably tapered 26, which provides the user with a location to exert precise controlled angular force on the front end 16. The back portion 12, middle portion 14 and the front portion 16 are preferably made of a one piece metal construction.

The middle portion 14 may be of uniform size, or may be adapted to taper in a direction which narrows towards the front portion 16. The middle portion 14 also provides a location on the handle 10 where the user can apply precise and controlled force to the front portion 16 which releasably secures the shaft of the dental attachment (not shown) in the transverse aperture 18. The middle portion 14 may extend straight along the centerline of the back portion in one embodiment, or may extend in a partial radius from fifteen degrees to forty-five degrees from the centerline of the back portion in an alternate embodiment. Either embodiment may be used in accordance with the disclosure provided herein.

The front portion 16 is larger than the middle portion 14 and is threaded 30 to threadably receive a threaded nut 20 thereon. The distal end 28 of the front portion 16 is preferably smaller than the threaded portion 30, and the distal end 28 is preferably inclined, radiused or tapered, as shown in FIG. 1 and FIG. 2.

The front portion 16 has a transverse aperture 18 extending through the threaded 30 front portion 16. The transverse aperture 18 is preferably 0.160 diameter, plus 0.002 inches, minus 0.000 inches. Other transverse aperture 18 sizes may be used, depending upon the size of the shaft of the dental tool selected. This enables the user to position the shaft of a selected dental tool attachment from either end of the transverse aperture 18. This is important where the middle portion 14 is partially radiused, as shown in FIG. 2.

The threaded nut 20 is preferably a No. ¼-20-UNS-2B nut, 0.31 inches long. Other thread and nut sizes may be used without departing from the spirit of this disclosure, or from the scope of the following claims.

The shaft of the selected dental attachment is inserted in a desired position into one end of the transverse aperture 18, and the threaded nut 20 is tightened against the side of the shaft of the dental attachment tool, to releasably secure the dental attachment within the transverse aperture 18. The threaded nut 20 preferably has a textured gripping surface 32 for ease of rotation by the user's fingers. The textured gripping surface may be knurled, ribbed or otherwise roughened to improve the finger gripping surface.

FIG. 2 depicts the handle apparatus having a partially radiused middle portion 14. The partially radiused "R" middle portion provides the user with an alternative embodiment for reaching into areas of the mouth that would be difficult or impossible to reach with a straight middle portion 14.

The partially radiused middle portion 14 is preferably radiused from one and one-half inches to two and one-half inches in length, and radiused "R" to incline from fifteen degrees to forty five degrees from the centerline of the back portion 12, as shown in FIG. 2. Most preferably, the partially radiused middle portion 14 is radiused "R" to incline thirty degrees from the centerline of the back portion 12.

The handle apparatus 10 may be made of any suitable metal, such as steel, stainless steel, aluminum, brass, etc. The handle apparatus 10 is preferably made of 6061T651 aluminum rod. The aluminum rod is preferably selected from 3/16 inch rod to 3/4 inch rod, with 1/4 inch rod being most preferred. The length of the handle apparatus 10 is preferably from five inches to 9 inches, with six to seven inches being most preferred.

In use, the handle apparatus 10 is positioned to receive the shaft of a desired dental attachment within the transverse aperture 18 located in the front portion 16 of the handle apparatus 10. Once positioned in the desired orientation in relation to the handle apparatus 10, the threaded nut 20 is tightened to abut the shaft of the selected dental tool attachment to releasably secure the dental attachment to the handle apparatus 10.

The user then grasps the back portion 12 and/or the middle portion 14 of the handle apparatus 10 to position and manipulate the dental attachment in the patient's mouth.

When the task is completed, or when a different dental attachment is desired, the user may quickly change dental attachments by threadably biasing the nut 20 away from the shaft of the dental tool. Once the nut has been loosened, the dental attachment may be removed from the transverse aperture 18, so that a different dental attachment may be inserted within the transverse aperture 18.

Once the shaft of the selected dental tool has been positioned and aligned within the transverse aperture 18, the nut 20 may once again be tightened against the inserted shaft portion of the dental attachment. In this way, many types of dental attachments may be used, without requiring a different handle apparatus 10.

While the handle apparatus disclosed herein has been disclosed for use in securing the shaft of a selected dental attachment, it is within the scope of this disclosure to use the handle apparatus 10 disclosed herein for other uses, such as for surgery, pottery, shaping, wood carving, sculpting, etching, etc., and such alternate uses are intended to be incorporated within the scope of the following claims.

Therefore, while this invention has been described with reference to a particular embodiment, it is to be understood that modifications may be made without departing from the spirit of this invention, or from the scope of the following claims.

Endodontic Instrument
10—handle apparatus
12—back portion
14—middle portion
16—front portion
18—transverse aperture
20—threaded nut
22—handle end
24—tapered middle portion
26—tapered front portion
28—distal end
30—threaded portion
32—textured gripping surface

What is claimed is:

1. An endodontic instrument apparatus for releasably securing a shaft of an endodontic dental tool, which comprises:

a) a back portion sized to be comfortably received within a user's hand, the back portion having a tapered handle end;

b) a middle portion sized to be smaller in cross-section than the back portion, with a tapered transition area extending between the back portion and the middle portion;

c) an externally threaded front portion of larger cross-sectional size than the middle portion, an transverse aperture extending through the externally threaded front portion, the transverse aperture sized to closely receive the shaft of the endodontic dental tool therein, the front portion further having a radiused distal end portion of a size smaller than the threaded front portion; and d) an internally threaded nut sized to be threadably received on the externally threaded front portion, the nut rotated to threadably bias the nut against the shaft on the selected endodontic tool positioned in the transverse aperture to securely and releasably secure the dental tool in the transverse aperture.

2. The endodontic instrument apparatus of claim 1, wherein the middle portion extends from one and one-half inches to two and one-half inches in length, and is partially radiused from fifteen to forty-five degrees from the centerline of the back portion.

3. The endodontic instrument apparatus of claim 1, wherein the middle portion extends from one and one-half inches to two and one-half inches in length, and extends straight along the centerline of the back portion.

4. The endodontic instrument apparatus of claim 1, wherein the back portion, the middle portion and the front portion are made of a one-piece metal construction.

5. The endodontic instrument apparatus of claim 1, wherein the one-piece metal construction is made of 3/16 inch to 3/4 inch 6061-T651 aluminum rod, from five inches to nine inches in length.

6. The endodontic instrument apparatus of claim 1, wherein the one piece metal construction is made of 1/4 inch aluminum rod, six and 1/2 inches long.

7. The endodontic instrument apparatus of claim 1, wherein the back portion is textured to provide an improved gripping surface.

8. The endodontic instrument apparatus of claim 1, wherein the external portion of the internally threaded nut is textured to provide an improved finger gripping surface.

9. The endodontic instrument apparatus of claim 1, wherein the transverse shaft is sized to be 0.160 inches in diameter, plus 0.002, minus 0.000 inches.

10. The endodontic instrument apparatus of claim 1, wherein the externally threaded front portion is 1/4-40 UNS-2A, and the internally threaded nut is 1/4-40 UNS-2B.

11. The endodontic instrument apparatus of claim 1, wherein the middle portion is of uniform cross-sectional size.

12. The endodontic instrument apparatus of claim 1, wherein the middle portion tapers to narrow towards the front portion.

13. The endodontic instrument apparatus of claim 1, wherein the back portion, the middle portion and the front portion are made of a one-piece metal construction.

14. The endodontic instrument apparatus of claim 1, wherein the one-piece metal construction is made of 3/16 inch to 3/4 inch 6061-T651 aluminum rod, from five inches to nine inches in length.

15. The endodontic instrument apparatus of claim 1, wherein the one piece metal construction is made of 1/4 inch aluminum rod, six to seven inches long.

16. The endodontic instrument apparatus of claim 1, wherein the back portion is textured to provide an improved gripping surface.

17. An endodontic instrument apparatus for releasably securing a shaft of a selected dental tool, which comprises:
   a) a back portion sized to be comfortably received within a user's hand;
   b) a middle portion sized to be smaller in cross-section than the back portion, with a tapered transition area extending between the back portion and the middle portion; the middle portion is partially radiused from fifteen to forty-five degrees from the centerline of the back portion;
   c) a front portion having a larger cross-sectional size than the middle portion, the front portion externally threaded, a transverse aperture extending through the externally threaded front portion, the transverse aperture sized to closely receive the shaft of a selected endodontic dental tool therein; and
   d) an internally threaded nut sized to be threadably received on the externally threaded front portion, the nut rotated to threadably bias the nut against the shaft on the selected endodontic tool positioned in the transverse aperture to securely and releasably secure the dental tool in the transverse aperature.

18. The endodontic instrument apparatus of claim 17, wherein the external portion of the internally threaded nut is textured to provide an improved finger gripping surface.

19. The endodontic instrument apparatus of claim 17, wherein the transverse shaft is sized to be 0.160 inches in diameter, plus 0.002, minus 0.000 inches.

20. The endodontic instrument apparatus of claim 17, wherein the threaded front portion is ¼-40 UNS-2A, and the nut is ¼-40 UNS-2B.

21. The endodontic instrument apparatus of claim 17, wherein the middle portion is of uniform cross-sectional size.

22. The endodontic instrument apparatus of claim 17 wherein the middle portion tapers to narrow towards the front portion.

23. An endodontic instrument apparatus for releasably securing a shaft of a selected endodontic dental tool, which comprises:
   b) a back portion sized to be three to five inches in length and 3/16 to ½ inches in diameter to be comfortably received within a user's hand;
   b) a middle portion sized to be smaller in cross-section than the back portion, with a tapered transition area extending between the back portion and the middle portion, the middle portion extending straight along the central axis of the back portion;
   c) a front portion having a larger cross-sectional size than the middle portion, the front portion externally threaded, a transverse aperture extending through the externally threaded front portion, the transverse aperture sized to closely receive the shaft of a selected endodontic dental tool therein, the front portion further having a radiused distal end portion of a size smaller than the externally threaded front portion; and
   d) an internally threaded nut sized to be threadably received on the externally threaded front portion, the nut rotated to threadably bias the nut against the shaft on the selected endodontic tool positioned in the transverse aperture to securely and releasably secure the dental tool in the transverse aperature.

24. The endodontic instrument apparatus of claim 23, wherein the back portion, the middle portion and the front portion are made of a one-piece aluminum construction.

* * * * *